(12) United States Patent
Plumptre et al.

(10) Patent No.: US 10,238,807 B2
(45) Date of Patent: Mar. 26, 2019

(54) DRIVE MECHANISM AND INJECTION DEVICE HEREWITH

(71) Applicant: Sanofi, Paris (FR)

(72) Inventors: David Aubrey Plumptre, Worcestershire (GB); Simon Lewis Bilton, Warwickshire (GB)

(73) Assignee: Sanofi, Paris (FR)

( * ) Notice: Subject to any disclaimer, the term of this patent is extended or adjusted under 35 U.S.C. 154(b) by 211 days.

(21) Appl. No.: 14/915,441

(22) PCT Filed: Sep. 3, 2014

(86) PCT No.: PCT/EP2014/068656
§ 371 (c)(1),
(2) Date: Feb. 29, 2016

(87) PCT Pub. No.: WO2015/032783
PCT Pub. Date: Mar. 12, 2015

(65) Prior Publication Data
US 2016/0279338 A1    Sep. 29, 2016

(30) Foreign Application Priority Data

Sep. 3, 2013 (EP) .................... 13182765

(51) Int. Cl.
*A61M 5/315* (2006.01)
*A61M 5/20* (2006.01)

(52) U.S. Cl.
CPC .......... *A61M 5/31553* (2013.01); *A61M 5/20* (2013.01); *A61M 5/3157* (2013.01);
(Continued)

(58) Field of Classification Search
CPC .......... A61M 5/31553; A61M 5/31551; A61M 5/3157; A61M 5/31583
See application file for complete search history.

(56) References Cited

U.S. PATENT DOCUMENTS 533,575 A   2/1895  Wilkens
4,865,591 A   9/1989  Sams
(Continued)

FOREIGN PATENT DOCUMENTS

CA   2138528   2/1994
CA   2359375   7/2000
(Continued)

OTHER PUBLICATIONS

International Search Report and Written Opinion in International Application No. PCT/EP2014/068656, dated Feb. 17, 2015, 10 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

The present invention relates to a drive mechanism which is suitable for an injection device, especially a pen type drug delivery device. The mechanism includes a housing, a dosing member which during dose setting, dose resetting and dose dispensing rotates relative to the housing between a zero dose position and a maximum dose position, and an insert that is rotationally constrained to the housing. The dosing member and the insert each include at least one abutment feature contacting each other when the dosing member reaches its zero dose position during dose dispensing, and an audible and/or tactile feedback is generated by the contact of the abutment features.

18 Claims, 6 Drawing Sheets
Specification includes a Sequence Listing.

(52) U.S. Cl.
CPC .... *A61M 5/31578* (2013.01); *A61M 5/31583* (2013.01); *A61M 5/31535* (2013.01); *A61M 5/31541* (2013.01); *A61M 2205/581* (2013.01); *A61M 2205/582* (2013.01)

(56) References Cited

U.S. PATENT DOCUMENTS

| | | | |
|---|---|---|---|
| 5,092,842 | A | 3/1992 | Bechtold et al. |
| 5,226,895 | A | 7/1993 | Harris |
| 5,226,896 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,378,233 | A | 1/1995 | Haber et al. |
| 5,383,865 | A | 1/1995 | Michel |
| 5,391,157 | A | 2/1995 | Harris et al. |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,807,346 | A | 9/1998 | Frezza |
| 5,820,602 | A | 10/1998 | Kovelman et al. |
| 5,851,079 | A | 12/1998 | Horstman et al. |
| 5,921,966 | A | 7/1999 | Bendek et al. |
| 5,957,896 | A | 9/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,562,006 | B1 | 5/2003 | Hjertman et al. |
| 6,613,023 | B2 | 9/2003 | Kirchhofer et al. |
| 6,699,224 | B2 | 3/2004 | Kirchhofer et al. |
| 6,932,794 | B2 | 8/2005 | Giambattista et al. |
| 6,936,032 | B1 | 8/2005 | Bush, Jr. et al. |
| 7,169,132 | B2 | 1/2007 | Bendek et al. |
| 7,241,278 | B2 | 7/2007 | Moller |
| 7,678,084 | B2 | 3/2010 | Judson et al. |
| 8,187,233 | B2 | 5/2012 | Harms et al. |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0097883 | A1 | 5/2004 | Roe |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2007/0016143 | A1 | 1/2007 | Miller et al. |
| 2009/0012479 | A1* | 1/2009 | Moller ............... A61M 5/20 604/211 |
| 2009/0275916 | A1 | 11/2009 | Harms et al. |
| 2012/0277683 | A1* | 11/2012 | Moller ............. A61M 5/31551 604/189 |
| 2017/0095613 | A1* | 4/2017 | Moller ............. A61M 5/31551 |

FOREIGN PATENT DOCUMENTS

| | | |
|---|---|---|
| EP | 0496141 | 1/1991 |
| EP | 0730876 | 9/1996 |
| EP | 0897729 | 2/1999 |
| EP | 0937471 | 8/1999 |
| EP | 0937476 | 8/1999 |
| EP | 1776975 | 5/2002 |
| EP | 1974761 | 10/2008 |
| GB | 0304822.0 | 3/2003 |
| GB | 0304823.8 | 11/2017 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |
| WO | WO 03/080160 | 10/2003 |
| WO | WO2006/079481 | 8/2006 |
| WO | WO2006/084876 | 8/2006 |
| WO | WO2011/060785 | 5/2011 |
| WO | WO2011/060786 | 5/2011 |

OTHER PUBLICATIONS

International Preliminary Report on Patentability in International Application No. PCT/EP2014/068656, dated Mar. 8, 2016, 7 pages.
"Pen-injectors for medical use—Part 1: Pen-injectors—Requirements and test methods," International Standard, reference number: ISO 11608-1:2000(E), first edition Dec. 15, 2000, 32 pages.

* cited by examiner

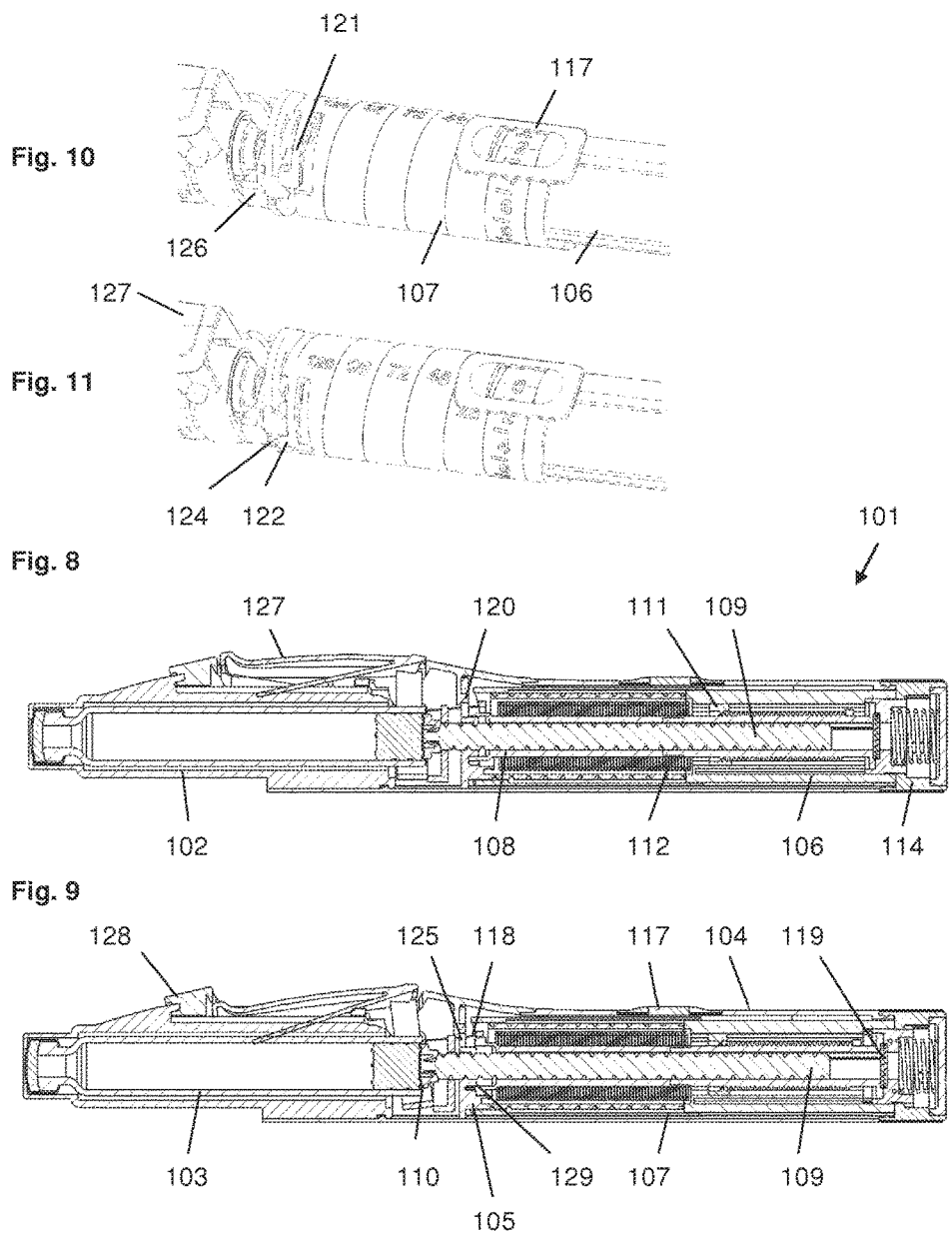

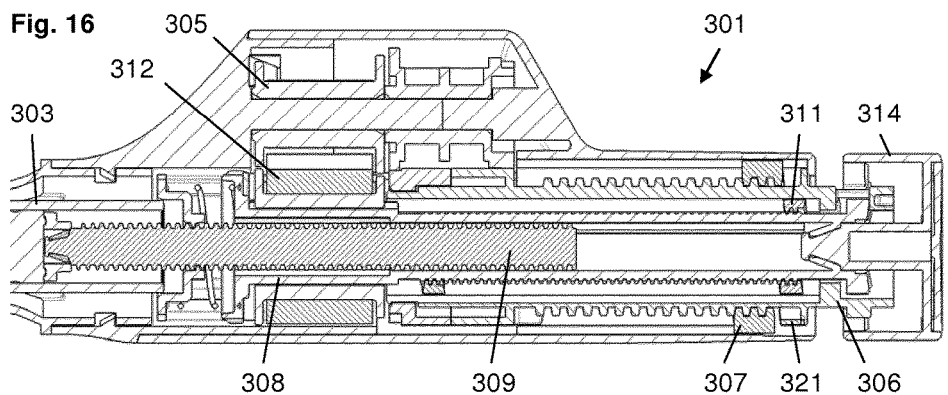
Fig. 16
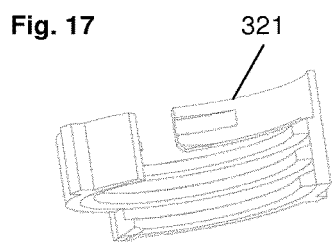
Fig. 17
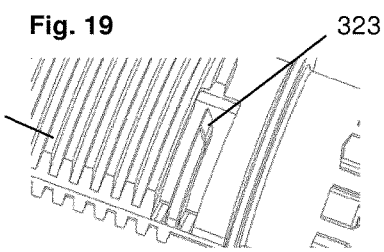
Fig. 19
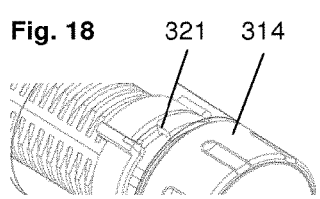
Fig. 18
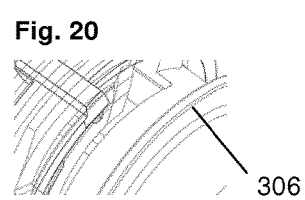
Fig. 20
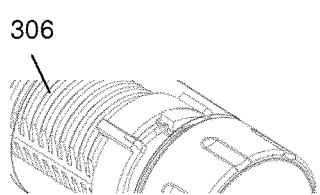
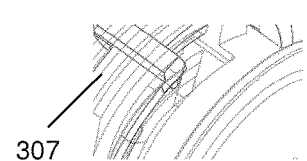
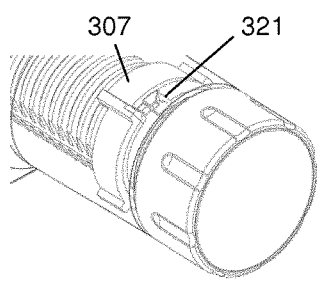
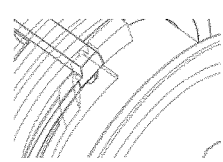

Fig. 21
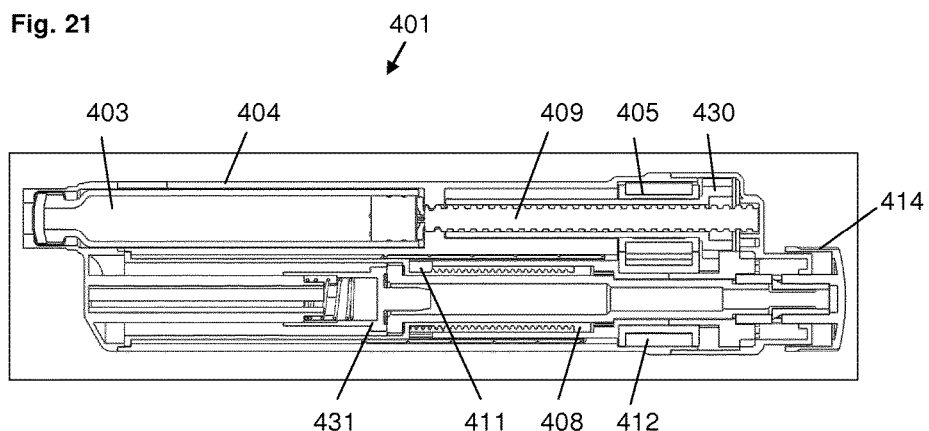
Fig. 22
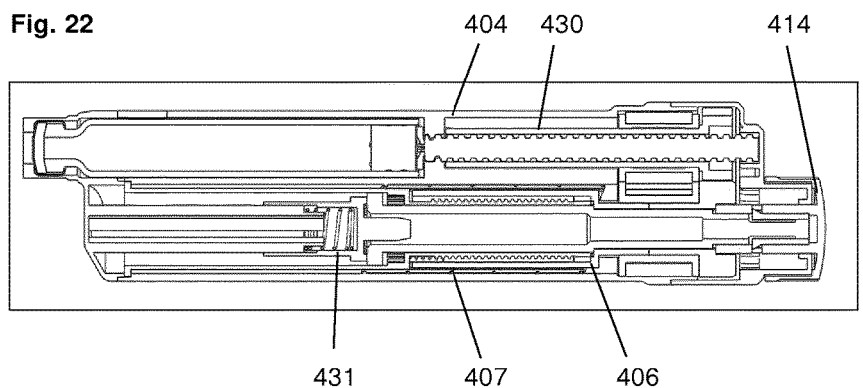
Fig. 23a Fig. 23b Fig. 23c
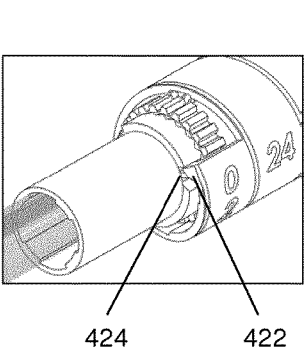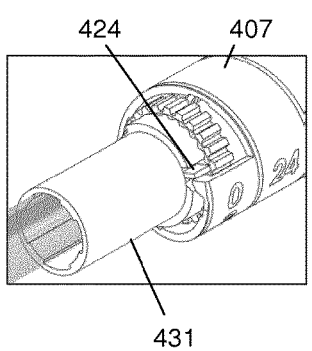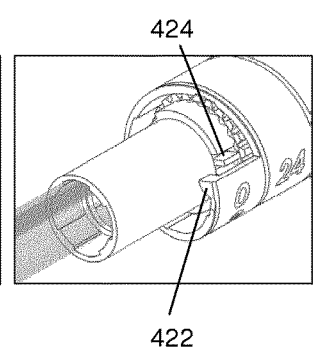

DRIVE MECHANISM AND INJECTION DEVICE HEREWITH

CROSS-REFERENCE TO RELATED APPLICATIONS

This application is a U.S. national stage application under 35 USC § 371 of International Application No. PCT/EP2014/068656, filed on Sep. 3, 2014, which claims priority to European Patent Application No. 13182765.1, filed on Sep. 3, 2013, the entire contents of which are incorporated herein by reference.

TECHNICAL FIELD

The present disclosure relates to a drive mechanism which is suitable for an injection device, especially a pen type drug delivery device.

BACKGROUND

In the following, the distal end of an injection device or drive mechanism is referred to as the end where a cartridge and e.g. a needle are located, whereas the opposite end is the proximal end. A dose button may be provided at the proximal end.

The general function of a drive mechanism as defined above is to set a dose and to subsequently dispense the set dose. Dose setting (dose dialling) usually requires a user to manipulate one element of the drive mechanism, preferably to rotate a dial member e.g. via a dial grip. During dose dispensing the dial member may move, e.g. rotate, back to its original position wherein a drive member, which is not actuated during dose setting is moved together with the dial member during dose dispensing. The movement of the drive member may be a rotation, a displacement in the distal direction or a combined movement e.g. along a helical path. The drive member may act on a piston rod, e.g. a lead screw, for expelling medicament from a cartridge during dose dispensing.

In addition to this basic function of a drive mechanism it is in some cases preferred to allow a resetting of an already set dose, i.e. a correction or a deselecting of a dose. Preferably the user simply has to rotate the dial member, e.g. via a dial grip, in the opposite direction compared to the rotation during dose setting. Preferably, the drive member is not actuated during dose resetting, either.

At the beginning of dose setting, the mechanism is usually in a zero dose position, i.e. the previous dose has been fully administered and no new dose has been dialed. The user may set a dose up to a maximum dose which is defined by the mechanism, for example by providing an end stop which prevents setting of a higher dose. Typically, a maximum settable dose is 60, 80, 100 or 120 units of a medicament. During dose resetting, an already set dose may be reduced down to the zero dose position of the device. It is important that a user fully dispenses the required set dose to avoid an underdose which may have serious medical consequences. Thus, it is required to indicate to a user that the mechanism is in its zero dose position after dose dispensing.

An injection device as defined above is known e.g. from EP 1 974 761 B1 wherein during dose setting, dose resetting and dose dispensing a dose grip and a dose dial sleeve rotate with respect to a housing and a housing insert between a zero dose position and a maximum dose position. A visual indication of the dose is provided by reference numerals on the outer surface of the dose dial sleeve. A window in the housing allows the visual indication of the dose currently dialed to be viewed.

In addition, a drive mechanism is known from EP 0 730 876 B1 which includes a housing and a dial. The dial is rotated during dose setting and axially displaced during dose dispensing. As the dial reaches its end of dose position (zero dose position), a finger of the dial moves past a housing edge and into a housing groove, which creates a click sound thereby providing an audible confirmation that the entire dosage has been injected. Further, WO 2006/079481 A1 discloses a similar mechanism, which provides a non-visual feedback signal to a user only at the end of injection of a set dose. This is achieved by providing two parts which perform a relative rotational movement during injection of a dose, wherein the two parts abut or engage thus causing the non-visual feedback signal. In some embodiments of WO 2006/079481 A1, the two parts may perform a relative rotation during dose setting, too. A relative rotation during dose resetting is not described. The mechanisms of EP 0 730 876 B1 and WO 2006/079481 A1 do not prevent that the click sound or non-visual feedback signal is generated during dose resetting. Thus, users may be confused if a signal is provided which indicates completion of the dose dispensing process even if the user did not initiate this dispensing process.

Further, WO 2011/060785 A1 discloses a scale with an end-of-dose ratchet arm. The scale rotates during dose setting, dose correction and dose dispensing. The housing comprises a stop rib which the ratchet arm passes just before the injection stops. This creates a clicking sound different from the sound of injection clicks. Further, scale is axially movable against the bias of flexible arms when the actuation button is pressed. The flexible arms displace the scale back after dose dispensing. This results in the end-of-dose ratchet arm not interfering with the stop rib during dose setting, i.e. when the actuation button is not depressed. A similar mechanism is known from WO 2011/060786 A1 disclosing a dispense clicker mechanism having a series of teeth on an inner side of the housing with one tooth having a different configuration. A ratchet arm is held in a position not interfering with the teeth during dose setting or dose correction and is moved axially to a position engaging teeth during dispensing. Tooth is located such that a different click is generated at the end of injection.

SUMMARY

Aspects of the present invention provide an improved alternative to the above solutions. Certain aspects of the present invention relate to a drive mechanism and an injection device giving a reliable feedback to users at the end of the dispensing process. Preferably, the mechanism does not generate a signal during dose resetting. The mechanism may include a housing and a dosing member, which during dose setting, dose resetting and dose dispensing rotates relative to the housing between a zero dose position and a maximum dose position. Further, this disclosure relates to an injection device comprising such a drive mechanism and a cartridge containing a medicament.

According to some aspects of the present invention, the mechanism further comprises an insert which is rotationally constrained to the housing. The dosing member and the insert each comprise at least one abutment feature which contact each other in the moment when the dosing member reaches its zero dose position during dose dispensing. This contact of the abutment features generates an audible and/or tactile feedback. In other words, the mechanism provides a tactile and/or audible signal to the user indicating that the mechanism reached its zero dose position at the end of the dose dispensing process. This tactile and/or audible signal may also be detected by visually impaired users. It is preferred if the abutment features contact each other only during dose dispensing, i.e. not during dose resetting, when the dosing member reaches its zero dose position. This avoids confusion for the users. Providing one of the abutment features on an insert may have the benefit of generating a feedback which is distinct from a feedback generated by the housing, e.g. during dose setting and/or dose resetting and/or dose dispensing.

Preferably, the drive mechanism further comprises an additional component part which is axially movable between a dose dispensing position and a dose setting and resetting position wherein the abutment features contact each other only when the additional component part is in its dose dispensing position. For example, the additional component part radially deflects one of the abutment features when the additional component part is in its dose dispensing position. In other words, the axial movement of the additional component part switches the mechanism between a mode in which reaching the zero dose position at the end of the dose dispensing process is indicated by a feedback signal and a mode in which reaching the zero dose position is not indicated by such a feedback, e.g. during dose resetting (dose correcting).

According to a first embodiment of the invention, the drive mechanism comprises an inner body rotationally constrained to the housing and a number sleeve which is in threaded engagement with the housing or the inner body. The number sleeve is movable between a zero dose position and a maximum dose position. The inner body comprises a flexible arm having a first abutment feature and the number sleeve comprises a corresponding second abutment feature contacting the first abutment feature when the number sleeve reaches its zero dose position during dose dispensing. Preferably, the number sleeve is a tubular component having a scale or numbers to visually indicate a set dose. The number sleeve may be directly actuated by a user or indirectly, e.g. via a dose dial grip and/or a dose setting member which is at least rotationally coupled to the number sleeve.

For the above mentioned first embodiment and all of the embodiments described below the abutment features (e.g. ramp features) and flexible arm features may be swapped between the two interacting components. For example, in an alternative to the first embodiment, the number sleeve may have the flexible arm with the first abutment feature and the inner body may have the second abutment feature.

According to a second embodiment of the invention, the drive mechanism comprises a trigger clutch rotationally constrained to the housing and a number sleeve which is in threaded engagement with the housing or an inner body. The number sleeve is movable between a zero dose position and a maximum dose position. The trigger clutch comprises a first abutment feature and the number sleeve comprises a corresponding second abutment feature contacting the first abutment feature when the number sleeve reaches its zero dose position during dose dispensing. The trigger clutch may be a component which is actuated by a trigger which is pressed or actuated to initiate dose dispensing. The trigger clutch may have the additional function of coupling and/or decoupling further components of the mechanism, e.g. a drive member and the housing or an inner housing body.

To ensure that in the two above embodiments the abutment features contact each other only during dose dispensing the number sleeve and its second abutment feature move on a helical path during dose setting, dose resetting and dose dispensing wherein the first abutment feature is in the helical path only during dose dispensing. This avoids unintended generation of a signal during dose resetting.

For the first embodiment this may be achieved by providing a drive member which is axially displaceable relative to the housing between a dose setting position and a dose dispensing position. Preferably, the first abutment feature is not in the helical path in an unstressed state of the flexible arm wherein in its dose dispensing position the drive member urges the flexible arm and its first abutment feature into the helical path. In other words as long as the drive member is not moved into its dose dispensing position, no signal could be generated because the abutment features do not contact each other even in the zero dose position of the mechanism. Only during dose dispensing, the mechanism is in a condition that allows contact of the abutment features and thus generation of the signal.

For the second embodiment this may be achieved in a similar manner by providing a trigger for axially displacing the trigger clutch relative to the housing between a dose setting position and a dose dispensing position, wherein the first abutment feature is not in the helical path in the dose setting position of the trigger clutch and wherein the trigger urges the trigger clutch and its first abutment feature in its dose dispensing position into the helical path.

As an alternative or in addition to the movement of the first abutment feature, the second abutment feature may be moved between a dose setting or dose resetting position and a dose dispensing position.

In the first and second embodiment, the mechanism may further comprise a torsion spring fixed between the housing and a dial member such that energy is accumulated in the torsion spring upon rotation of the dial member relative to the housing during dose setting, which energy is used to actuate a drive member during dose dispensing.

According to a third embodiment of the invention, the drive mechanism comprises a chassis rotationally constrained to the housing and a dial gear which is rotatable relative to the chassis between a zero dose position and a maximum dose position and which is axially displaceable relative to the chassis between a dose setting position and a dose dispensing position. Preferably the chassis comprises a first abutment feature and the dial gear comprises a corresponding second abutment feature contacting the first abutment feature when the dial gear reaches its zero dose position during dose dispensing. The dial gear may have the form of a ring or disk and may be provided with splines and/or teeth engaging further components of the mechanism. Further, the axial displacement of the dial gear, i.e. a displacement in the direction of the axis of rotation of the dial gear during dose setting, may couple and/or de-couple the dial gear to/from further components.

Preferably, the first abutment feature is a flexible finger provided on the chassis and the second abutment feature is a recess or a ramp on the dial gear. The flexible finger does not contact the recess or ramp in the dose setting position of the dial gear whereas the flexible finger contacts the recess or ramp in the dose dispensing position when the dial gear reaches its zero dose position. Thus, contact of the abutment features is prevented as long as the dial gear is in its dose setting position.

The mechanism may further comprise a compression spring acting on a piston rod or bung in a cartridge during dose dispensing. The spring may be coupled to a cable or belt which may initially be wound on a spool and which is unwound thus releasing the spring during dose dispensing. The spring may be pre-compressed during the manufacturing process such that the energy for dispensing the contents of the whole cartridge of medicament is stored in the spring.

According to a fourth embodiment of the invention, the drive mechanism comprises a dose nut, which is axially displaceable between a zero dose position and a maximum dose position and which is rotationally constrained to the housing. The mechanism further comprises a dial sleeve which is rotatable relative to the housing. The dose nut may comprise a flexible finger with a first abutment feature, which is deflected during dose dispensing and which hits a second abutment feature provided on the dial sleeve when the dose nut reaches its zero dose position.

As an alternative, according to a fifth embodiment of the invention, the drive mechanism comprises a dose nut, which is axially displaceable between a zero dose position and a maximum dose position and which is rotationally constrained to the housing, and a dial sleeve which is rotatable relative to the housing, wherein the dial sleeve comprises a flexible finger with a first abutment feature, which is deflected during dose dispensing and which hits a second abutment feature provided on the dose nut when the dose nut reaches its zero dose position.

Preferably, the dose nut of the fourth and fifth embodiment is a full nut or a half nut threadedly engaged with the dial sleeve. The dose nut may be splined to the housing to allow an axial displacement of the dose nut relative to the housing but preventing a relative rotational movement. The axial displacement of the dose nut may be limited by two stops, which might be the ends of the helical track or separate stop elements, defining the zero dose position and the maximum dose position. Preferably, the dial sleeve rotates during dose setting, dose resetting and dose dispensing such that the dose nut due to the threaded interface with the dial sleeve travels in the helical path of the threaded interface. Further rotation of the dial sleeve is limited by the dose nut abutting one of the two stops in the zero dose position and the maximum dose position. In other words, the zero dose position and the maximum dose position of the dial sleeve is defined by the number of rotations allowed by position of dose nut in helical track of dial sleeve.

According to a sixth embodiment of the invention, the drive mechanism comprises a clicker rotationally constrained to the housing and a number sleeve which is in threaded engagement with the housing or an inner body and movable between a zero dose position and a maximum dose position. The clicker comprises a first abutment feature and the number sleeve comprises a corresponding second abutment feature contacting the first abutment feature when the number sleeve reaches its zero dose position during dose dispensing.

Preferably, the number sleeve and its second abutment feature move on a helical path during dose setting, dose resetting and dose dispensing whereas the clicker is axially displaceable relative to the housing such that the first abutment feature is in the helical path only during dose dispensing. Thus, only during dose dispensing, the mechanism is in a condition that allows contact of the abutment features and hence generation of the signal. The clicker may be an element which causes together with a further component, e.g. an inner body, the number sleeve, a dial member or the like, a click sound during dose setting and/or dose resetting. For this purpose, the clicker may be provided with splines, notches or teeth which override corresponding features of the further component. During dose setting and/or dose resetting, the clicker may shuttle axially as the splines, notches or teeth override the corresponding features.

According to one aspect of this embodiment, the drive mechanism further comprises a dial grip sleeve which is axially displaceable relative to the housing between a dose setting position and a dose dispensing position. The first abutment feature is not in the helical path in the dose setting position of the dial grip sleeve whereas in its dose dispensing position the dial grip sleeve axially displaces the clicker to urge its first abutment feature into the helical path.

According to a further aspect of this embodiment, a cartridge and a piston rod acting on a bung in the cartridge may be provided parallel and spaced from the clicker and the number sleeve. A meshing gear interface may be provided for transmitting torque between a driven member on the cartridge side and a drive member on the number sleeve side.

The mechanism of the fourth, fifth and sixth embodiment may further comprise a flat spring or tensioning element acting on a drive member during dose dispensing. The flat spring or tensioning element may initially be wound on a spool and which is unwound onto a second spool thus releasing the flat spring or tensioning element during dose dispensing. The flat spring or tensioning element may be pre-wound during the manufacturing process such that the energy for dispensing the contents of the whole cartridge of medicament is stored in the flat spring or tensioning element.

To allow rotation of components of the mechanisms according to the above embodiments, it is preferred if the components are mainly located concentrically about a common longitudinal axis of the drive mechanism. Thus, the components may have a tubular or sleeve-like shape. For example, the nut, the drive member and the dial may each be a tubular element with the nut surrounding the drive member and the dial member surrounding the nut (and thus the drive member). As an alternative, the nut may be designed as a half-nut, i.e. a ring segment.

Further, although it is desirable to reduce the total number of components of a drive mechanism, it might be useful for manufacturing reasons to split one or more components into separate elements. For example, a housing may comprise an outer body and an insert and/or an inner body which is axially and/or rotationally constrained to the outer body. In addition, a clutch may be designed by providing protrusions and/or recesses directly on the components which are to be coupled or decoupled by the clutch. As an alternative, a separate clutch element may be provided interposed between the two components which have to be coupled or decoupled.

Some aspects of the present invention are directed to drive mechanisms which may be used in injection devices. An injection device usually further comprises a cartridge holder and a cartridge containing medicament to be dispensed. In a reusable injection device, the cartridge holder may be detachable from the drive mechanism to exchange an empty cartridge by a new one. As an alternative, in a disposable injection device the cartridge holder and the cartridge are firmly attached to the drive mechanism such that the whole injection device has to be discarded after a number of doses have been dispensed from the cartridge.

In some aspects, an injection device may comprise a drive mechanism as mentioned above and a cartridge containing a medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O)2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4 (1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (So-matropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Certain aspects of the present invention will now be described in further detail with reference to the accompanying schematic drawings, wherein FIG. 8 shows a section view of an injection device comprising a drive mechanism according to a second embodiment of the invention during dose setting, FIG. 9 shows a section view of the injection device of FIG. 8 during dose dispensing, FIG. 10 shows a detail of the drive mechanism of FIG. 8 during dose dispensing prior to the zero dose position, FIG. 11 shows a detail of the drive mechanism of FIG. 8 during dose dispensing at the zero dose position, FIG. 16 shows a section view of an injection device comprising a drive mechanism according to a fourth embodiment of the invention during dose setting, FIG. 17 shows a detail of the drive mechanism of FIG. 16, FIG. 18 shows a sequence of details of the drive mechanism of FIG. 16 during dose dispensing prior to and at the zero dose position, FIG. 19 shows a detail of the drive mechanism of a fifth embodiment of the invention during dose setting, FIG. 20 shows a sequence of details of the drive mechanism of FIG. 19 during dose dispensing prior to and at the zero dose position, FIG. 21 shows a section view of an injection device comprising a drive mechanism according to a sixth embodiment of the invention during dose setting, FIG. 22 shows a section view of the injection device of FIG. 21 during dose dispensing, FIG. 23a-c show a sequence of details of the drive mechanism of FIG. 21 in the dose dialing mode (FIG. 23a) and during dose dispensing prior to (FIG. 23b) and at (FIG. 23c) the zero dose position.

DETAILED DESCRIPTION

Figure 1:
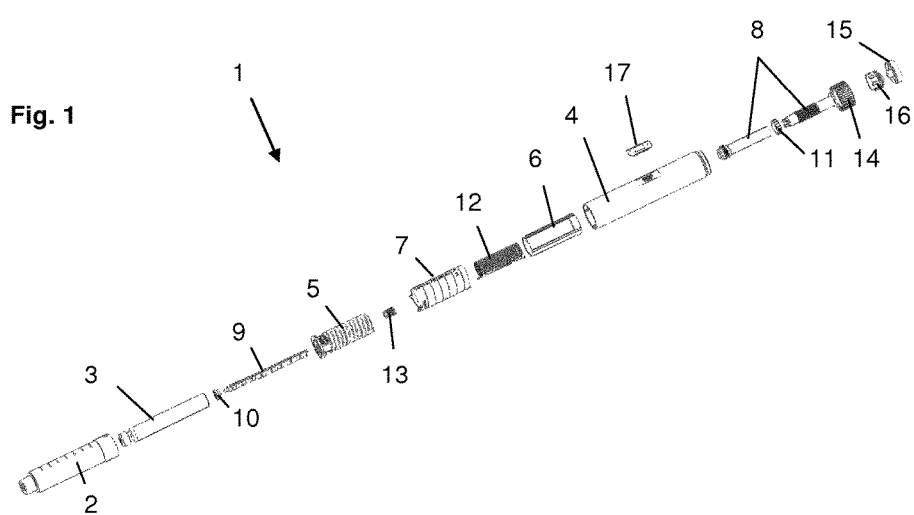
FIG. 1 shows an exploded view of an injection device comprising a drive mechanism according to a first embodiment of the invention.

An injection device 1 according to some aspects of the present invention is shown in FIG. 1 in an exploded view. The injection device 1 comprises a cartridge holder 2, a cartridge 3 and a drive mechanism. The drive mechanism comprises an outer housing 4, an inner housing 5, a dose dial sleeve as a dial member 6, a number sleeve as a display member 7, a drive sleeve as a drive member assay 8, a lead screw 9, a bearing 10, a nut 11, a drive spring 12, a return spring 13, a dial grip 14, a dose button 15 and a clutch plate 16. All components are located concentrically about a common principle axis of the mechanism. In more detail, the drive member assay 8 surrounds the lead screw 9, the torsion spring 12 surrounds the drive member 8, the dial member 6 and the inner housing 4 surround the torsion spring 12, the display member 7 surrounds the dial member 6 and the outer housing 4 surrounds the display member 7. Further, the nut 11 and the clutch plate 16 are located between the drive member assay 8 and the dial member 6. The drive member assay 8 is depicted comprising two components, which are rigidly fixed together. As an alternative, an integrally formed drive member 8 may be provided. Thus, in the following reference is made to drive member 8 meaning either an integrally formed or a two-part drive member.

Figure 2:
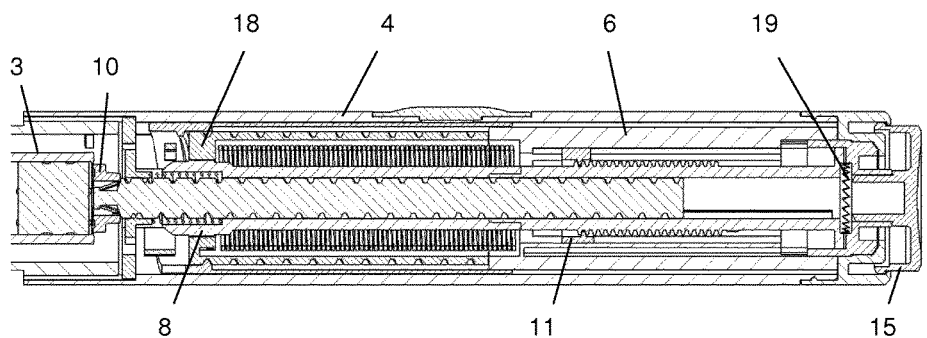
FIG. 2 shows a section view of the drive mechanism of FIG. 1 during dose setting.

The dose button 15 is axially constrained to the clutch plate 16. As can be seen in FIG. 2, this may be achieved by a snap-on connection with the clutch plate 16 having an opening for receiving a pin of the dose button 15. Thus, the dose button 15 may be rotatable with respect to the clutch plate 16.

Figure 3:
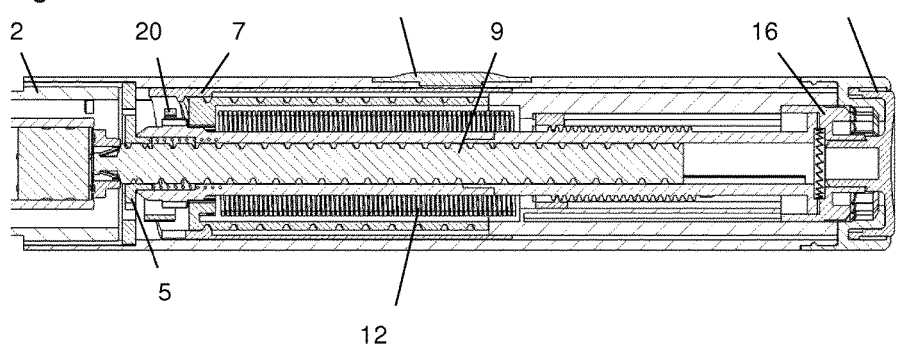
FIG. 3 shows an enlarged section view of the drive mechanism of FIG. 1 during dose dispensing.
Figure 4:
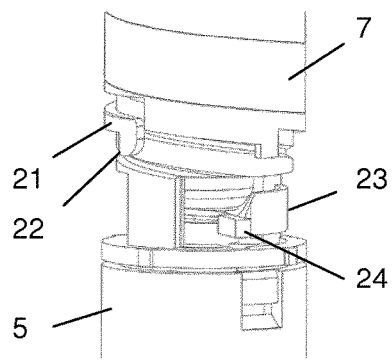
FIG. 4 shows a detail of the drive mechanism of FIG. 1 during dose setting.
Figure 5:
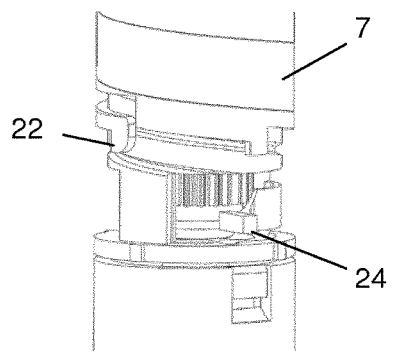
FIG. 5 shows a detail of the drive mechanism of FIG. 1 during dose dispensing.

The dial grip 14 is axially constrained to the outer housing 4 which forms a body for the drive mechanism. Again, as shown in FIG. 3, this may be achieved by a snap-on connection between the dial grip 14 and the outer housing 4. The dial grip 14 is rotationally constrained to the clutch plate 16. In the embodiment of FIGS. 1 to 6 a splined interface is provided between the dial grip 14 and the clutch plate 16. This splined interface is disconnected when the dose button 15 is pressed, i.e. when the dose button 15 and the clutch plate 16 are moved axially relative to the dial grip 14 and the outer housing 4.

The clutch plate 16 is further rotationally constrained to the dial member 6. Again, a splined interface may be provided between the clutch plate 16 and the dial member 6. The clutch plate 16 is further coupled to the drive member 8 via a ratchet interface which occurs on axial abutment. The ratchet interface provides a detented position between the dial member 6 and the drive member 8 corresponding to each dose unit and engages different ramped tooth angles during clockwise and anti-clockwise relative rotation between the dial member 6 and the drive member 8. This ratchet interface forms the second clutch 19 with corresponding teeth provided on the clutch plate 16 and the drive member 8, respectively.

The display member 7 is rotationally constrained to the dial member 6. Again, a splined interface may be provided between the display member 7 and the dial member 6. The display member 7 is further constrained to move along a helical path relative to the inner housing 5. This may be achieved by a threaded interface between the display member 7 and the inner housing 5. As an alternative, a threaded interface may be provided between display member 7 and the outer housing 4. The display member 7 is limited to move between a zero dose position (distal position) and a maximum dose position (proximal position) which are defined by end stops, e.g. in the outer housing 4. As shown in FIGS. 4 to 7 in more detail, the display member 7 has at its distal end a flexible arm 21 which is provided with an abutment feature 22 at its free end.

The display member 7 is marked with a sequence of numbers which are visible through a window 17 in the outer housing 4. As an alternative to a transparent window an aperture could be provided in the outer housing 4. The window 17 allows the user to denote the dialed dose of medicament. The window 17 may be or may comprise a magnifying lens. The window 17 may be an integral part of the outer housing 4 or a separate component attached to the housing.

The nut 11 acts as a last dose nut and is interposed between the dial member 6 and the drive member 8. The nut 11 is rotationally constrained to the dial member 6, e.g. via a splined interface. Thus, the nut 11 may be axially displaced relative to the dial member 6. The nut 11 moves along a helical path relative to the drive member 8, e.g. via a threaded interface, when relative rotation occurs between the dial member 6 and the drive member 8, i.e. during dose setting and dose resetting. In an alternative embodiment, the nut 11 may be splined to the drive member and threaded to the dial member. An end stop (not shown) may be provided to limit the movement of the nut 11 in the track defined by the threaded interface.

The drive member 8 extends from the interface from the dial member 6 down to a splined tooth interface with the inner housing 5. This provides rotational constraint of the drive member 8 to the inner housing 5. The releasable splined tooth interface between the drive member 8 and the inner housing 5 forms the first clutch 18 with teeth provided on the dial member 6 and the drive member 8, respectively.

When the dose button 15 is pressed, the splined teeth of the first clutch 18 are disengaged and a ratchet feature 20 is engaged which provides an audible and/or tactile feedback during dose dispensing.

The inner housing 5 is rigidly fixed to the outer housing 4. Thus, neither any rotation nor any axial movement between the inner housing 5 and the outer housing 4 is possible. The inner housing 5 and the outer housing 4 may be formed as one integral part, however due to manufacturing reasons it is preferred to provide the housing as the two separate components of the outer housing 4 and the inner housing 5. As shown in FIGS. 4 to 7 in more detail, the inner housing 5 is provided with a flexible arm 23 having an abutment feature 24 at its free end.

The drive spring 12 is a torsion spring which is attached at one end to the inner housing 5 and at the other end to the dial member 6. The drive spring 12 is pre-wound upon assembly, such that it applies a torque to the dial member 6 when the mechanism is at zero units dialled. The action of rotating the dial grip 14 to set a dose rotates the dial number 6 relative to the inner housing 5 and winds up the drive spring 12.

The lead screw 9 is rotationally constrained to the drive member 8 e.g. via a splined interface. When rotated, the lead screw 9 is forced to move axially relative to the drive member 8. This is achieved by a threaded interface between the lead screw 9 and the inner housing 5. The bearing 10 is axially constrained to the lead screw 9 and acts on the bung within the cartridge 3 during dose dispensing.

The axial position of the drive member 8, the clutch plate 16 and the dose button 15 is defined by the action of the return spring 13 which abuts the inner housing 5 and applies a force on the drive member 8 in the proximal direction. This ensures that the clutch plate 16 is in splined engagement with the dial grip 14 and that the drive member 8 is in splined engagement with the inner housing 5. The return spring 13 also acts to maintain the engagement of the ratchet features between the drive member 8 and the clutch plate 16, i.e. to maintain the engagement of a second clutch 19 [comment: I'm not sure it's a problem but the second clutch has not yet been described at this point.]. As an alternative, the function of the return spring 13 may be achieved fully or in part by the torsion spring 12.

The outer housing 4 provides location for the cartridge 3 and the cartridge holder 2 which can be attached to the outer housing 4. Further, the outer housing 4 comprises an interface to rigidly constrain the inner housing 5 and a groove on its external surface to axially retain the dial grip 14. Further, a removable cap may be provided which fits over the cartridge holder 2 and is retained via clip features.

In the following, the functions and interactions of the above mentioned components will be described in more detail together with an explanation of the use of the drive mechanism of the injection device 1.

FIGS. 2 and 3 and FIGS. 4 and 5 show the drive mechanism during dose setting and dose dispensing, respectively. As explained above, when the dose button 15 is depressed and the drive member 8 moves axially, it acts on the flexible arm 23 on the inner housing 5 moving it radially outwards. In other words, in the unstressed condition of the flexible arm 23 (during dose setting and dose resetting), the arm 23 and its abutment feature 24 are in a radially inner position and are pushed outwards to a radially outer position during dose dispensing. For this purpose, the distal end of the drive member 8 may comprise a tapered or flared portion as shown in the Figures. The radially inner position of abutment feature 24 is chosen such that the abutment feature 22 of the display member 7 does not contact abutment feature 24 irrespective of the position of the display member 7.

Figure 6:
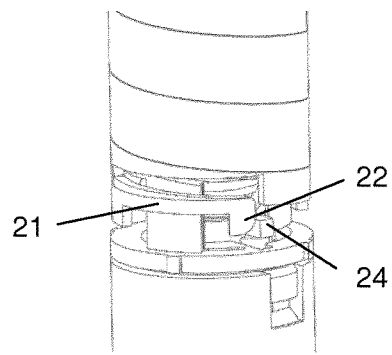
FIG. 6 shows a detail of the drive mechanism of FIG. 1 during dose dispensing prior to the zero dose position.
Figure 7:
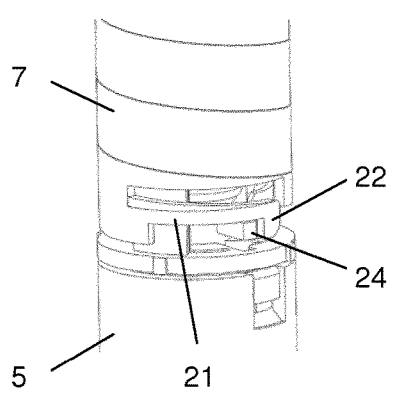
FIG. 7 shows a detail of the drive mechanism of FIG. 1 during dose dispensing at the zero dose position.
Figure 12:
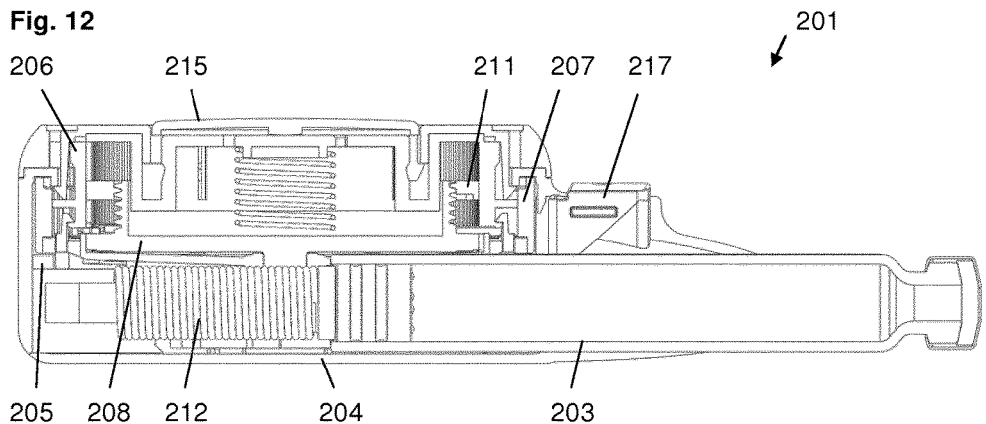
FIG. 12 shows a section view of an injection device comprising a drive mechanism according to a third embodiment of the invention during dose setting.
Figure 13:
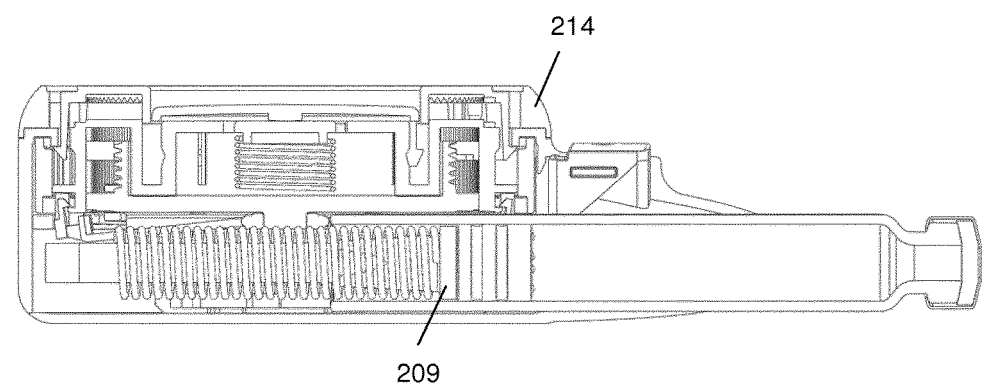
FIG. 13 shows a section view of the injection device of FIG. 12 during dose dispensing.
Figure 14:
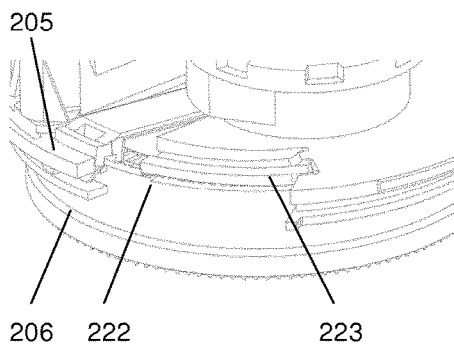
FIG. 14 shows a detail of the drive mechanism of FIG. 12 during dose dispensing prior to the zero dose position.
Figure 15:
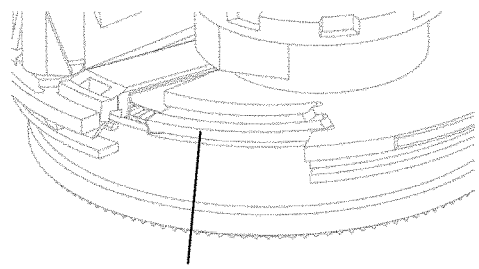
FIG. 15 shows a detail of the drive mechanism of FIG. 12 during dose dispensing at the zero dose position.

FIGS. 6 and 7 show approaching the end of a dose during dose dispensing. As the display member 7 returns to its zero dose position (distal position), the flexible click arm 21 with its abutment feature 22 rides over the inner housing flexible arm 23 and its abutment feature 24, creating an audible click. As the inner housing flexible arm 23 is only moved outwards during dispense, the setting torque is not affected and no click is created when dialling down to zero units during dose resetting.

Regarding the first clutch 18 and the second clutch 19 there are two generally distinct states of the drive mechanism of the injection device 1 which are shown in FIGS. 2 and 3, respectively. FIG. 2 shows the drive mechanism in an at rest condition which is a condition if a user does not exert any forces on the drive mechanism. In this at rest condition the first clutch 18 couples the drive member 8 to the inner housing 5 and the second clutch 19 allows a relative rotation between the clutch plate 16 and the drive member 8. However, to rotate the clutch plate 16 with respect to the drive member 8, a torque has to be provided to overcome the resistance of the ratchet feature, i.e. the clutch plate 6 is not freely rotatable with respect to the drive member 8. The second condition which is shown in FIG. 3 occurs if a user depresses dose button 15. This decouples the first clutch 18 such that the drive member 8 is free to rotate with respect to the inner housing 5 and the second clutch 19 is coupled to prevent a relative rotation between the drive member 8 and the clutch plate 16.

With the device in the at rest condition, the display member 7 is positioned against its zero dose abutment with the inner housing 5 and the dose button 15 is not depressed. A dose marking "0" on the dial member 7 is visible through the window 17 on the outer housing 4. The drive spring 12 which has a number of pre-wound turns applied to it during assembly of the device applies a torque to the dial member 6. The dial member 6 is prevented from rotating under the action of the torque by its ratchet interface (second clutch 19) with the drive member 8. The drive member 8 is prevented from rotating by the interlock provided by the engagement of splined teeth on the drive member 8 and the inner housing 5 (first clutch 18). Return spring 13 maintains the first clutch 18 in its coupled state by pushing the drive member 8 in the proximal direction. However, the drive member 8 is free to be displaced in the distal direction against the force of the return spring 13 as the teeth of the second clutch 19 override each other upon a relative rotation between the drive member 8 and the clutch plate 16. The height of the teeth of the second clutch 19 is smaller than the axial height of the splines of the first clutch 18. Thus, the first clutch 18 remains in its coupled state even if the teeth of the second clutch 19 override each other.

The user selects a variable dose of medicament by rotating the dial grip 14 clockwise which generates an identical rotation in the dial member 6. Rotation of the dial member 6 causes wind up of the drive spring 12, increasing the energy stored within it. The drive member 8 is still prevented from rotating due to the engagement of its splined teeth with the inner housing 5 (first clutch 18 coupled). A relative rotation must therefore occur between the clutch plate 16 and the drive member 8 via the ratchet interface of the second clutch 19.

The user torque required to rotate the dial grip 14 is a sum of the torque required to wind up the drive spring 12 and the torque required to overhaul the ratchet feature of the second clutch 19. The return spring 13 is designed to provide an axial force to the ratchet feature and to bias the components (drive member 8, clutch plate 16, dose button 15) away from the cartridge end of the injection device 1. The axial load acts to maintain engagement of the ratchet teeth of the clutch plate 16 and the drive member 8. The torque required to overhaul the ratchet teeth is resultant from the axial load applied by the return spring 13, the clockwise ramp angle of the ratchet, the friction coefficient between the mating surfaces and the mean radius of the ratchet features.

As the user rotates the dial grip 14 sufficiently to increment the mechanism by one unit, the dial member 6 rotates relative to the drive member 8 by one set of ratchet teeth. At this point the ratchet teeth reengage into the next detented position. An audible click is generated by the ratchet reengagement, and tactile feedback is given by the change in torque input required. Thus, the second clutch 19 forms a ratchet clicker.

Relative rotation of the dial member 6 and the drive member 8 causes a last dose nut 11 to travel along its threaded path towards its last dose abutment on the dial member 6. Rotation of the dial member 6 further generates rotation in the display member 7, which travels along its helical path defined by its interface with the inner housing 5. The dose marking corresponding to x units become aligned to the window 17 in the outer housing 4. The device is now set to deliver x units of liquid medicament.

With no user torque applied to the dial grip 14, the dial member 6 is now prevented from rotating under the action of the torque applied by the drive spring 12, solely by the ratchet engagement between the clutch plate 16 and the drive member 8 (second clutch 19). The torque necessary to overhaul the ratchet in the anti-clockwise direction is resultant from the axial load applied by the return spring 13, the anti-clockwise ramp angle of the ratchet, the friction coefficient between the mating surfaces and the mean radius of the ratchet features. The torque necessary to overhaul the ratchet must be greater than the torque applied to the dial member 6 (and hence clutch plate 16) by the drive spring 12. The ratchet ramp angle is therefore increased in the anti-clockwise direction to ensure this is the case.

The user may now choose to increase the selected dose by continuing to rotate the dial grip 14 in the clockwise direction. The process of overhauling the ratchet interfaces between the dial member 6 and the drive member 8 is repeated for each dose unit. Additional energy is stored within the drive spring 12 for each dose unit and audible and tactile feedback is provided for each unit dialed by the reengagement of the ratchet teeth. The torque required to rotate the dial grip 14 increases as the torque required to wind up the drive spring 12 increases. The torque required to overhaul the ratchet in the anti-clockwise direction must therefore be greater than the torque applied to the dial member 6 by the drive spring 12 when the maximum dose has been reached.

If the user continues to increase the selected dose until the maximum dose limit is reached, the display member 7 engages with its maximum dose abutment on the outer housing 4, which prevents further rotation of the display member 7, dial member 6, clutch plate 16 and dial grip 14. At this point the maximum dose marking on the display member 7 is aligned to the window 17 in the outer housing 4.

Depending on how many units have already been delivered by a drive mechanism, during selection of a dose, the last dose nut 11 may contact its last dose abutment, i.e. the end stop with the dial member 6. The abutment prevents further relative rotation of the dial member 6 and the drive member 8 and therefore limits the dose that can be selected. The position of the last dose nut 11 is determined by the total number of relative rotations between the dial member 6 and the drive member 8, which have occurred each time the user sets a dose.

With the mechanism in a state in which a dose has been selected, the user is able to deselect or reset any number of units from this dose. Deselecting a dose is achieved by the user rotating the dial grip 14 anti-clockwise. The torque applied to the dial grip 14 by the user is sufficient, when combined with the torque applied by the drive spring 12 to overhaul the ratchet 19 between the clutch plate 16 and the drive member 8 in the anti-clockwise direction. tion. When the ratchet is overhauled, anti-clockwise direction occurs in the dial member 6 (via the clutch plate 16) which returns the display member 7 towards the zero dose position, and unwinds the drive spring 12. The relative rotation between the dial member 6 and the drive member 8 causes the last dose nut 11 to return along its helical path, away from the last dose abutment.

With the mechanism in a state in which a dose has been selected, the user is able to activate the drive mechanism to commence delivery of a dose (dose dispensing). Delivery of a dose is initiated by the user depressing the dose button 15 on the top (proximal end) of the drive mechanism. When the dose button is depressed, it moves axially, acting on the clutch plate 16, which in turn acts on the drive member 8. The clutch plate 16 disengages its spline teeth from the dial grip 14 and after that the drive member 8 disengages its spline teeth (first clutch 18) from the inner housing 5.

When the splined interface of the first clutch 18 between the inner housing 5 and the dive member 8 disengages, the interface which prevents rotation of the drive member 8 during selection of a dose is removed. The torque applied to the dial member 6 from the drive spring 12 is transmitted, via the ratchet interface of the second clutch 19 into the drive member 8. This torque causes the drive member 8 and hence, due to its relative engagement with the inner housing 5, advancement of the lead screw 9. Axial displacement of the lead screw 9 forces liquid medicament to be delivered from the mechanism, by the action of the bearing 10 which contacts and displaces the bung within the cartridge 3.

The ratchet feature 20 of the inner housing 5 comprises a clicker arm (not shown). The clicker arm is a compliant cantilever beam integrated into the inner housing 5, which interfaces radially with the spline ratchet teeth in the drive member 8. The ratchet teeth 18b spacing corresponds to the drive member 8 rotation required to deliver a single dose unit. During dispense, as the drive member 8 rotates, the spline features engage with the clicker arm to produce an audible click with each dose unit delivered. The torque required to overhaul the clicker arm is resultant from the ratchet teeth profile, the stiffness of the cantilever beam and the nominal interference between the clicker arm and the ratchet. The clicker arm interface is designed such that the torque required to overhaul is significantly less than the torque provided by the drive spring 12.

The rotation of the dial member 6 also causes the display member 7 to return along its helical path, relative to the inner housing 5, towards the zero dose abutment. Delivery of a dose continues via the mechanical interactions described above while the user continues to depress the dose button 15. If the user releases the dose button 15, the return spring 13 returns the dose button 15 to its at rest position via the drive member 8 and the clutch plate 16 such that the drive member 8 becomes rotationally constrained and delivery of a dose is halted.

With the dose button 15 depressed, delivery of a dose continues until the display member 7 reaches its zero dose abutment with the inner housing 5. The torque applied to the dial member 6 is reacted by the abutment of the display member 7 and the dial member 6, wherein the clutch plate 16 and the drive member 8 are prevented from rotating further. During delivery of a dose, the drive member 8 and the dial member 6 rotate together, so that no relative motion in the last dose nut 11 occurs. The last dose nut 11 therefore travels towards its abutment on the dial member 6 during dose setting only and travels away from the end stop during dose resetting.

Once the delivery of a dose is stopped by the display member 7 returning to the zero dose abutment, the user may release the dose button 15 which will reengage the first clutch 18 between the inner housing 5 and the drive member 8. The mechanism is now returned to the at rest condition.

It is possible to angle the spline teeth on either the drive member 8 or inner housing 5 so that when the dose button 15 is released the reengagement of the spline teeth fractionally backwind the drive member 8 thereby removing the engagement of the display member 7 to the zero dose stop abutment in the inner housing 5. This removes the effect of clearances in the drive mechanism (for example due to tolerances) which could otherwise lead to slight advancement of the lead screw 9 and medicament dispense when the drive mechanism is dialled for the subsequent dose. This is due to the zero dose stop of the display member 7 no longer restraining the mechanism and instead the restraint returning to the splines between the drive member 8 and the inner housing 5.

A second embodiment of a drive mechanism which is suitable for an injection device 101 is shown in FIGS. 8 to 11. The injection device 101 comprises a cartridge holder 102, a cartridge 103 containing a medicament, optionally a cap (not shown) and a drive mechanism. The drive mechanism comprises an outer housing 104 with a window 117, an inner housing 105, a dial member 106 (dial sleeve), a display member 107 (number sleeve), a drive member 108 (drive sleeve), a lead screw 109, a bearing 110, a nut 111, a torsion spring 112, a dial grip 114, a first clutch 118, a second clutch 119 (clutch plate), a ratchet feature 120, a clutch spring 125, a trigger clutch 126, a trigger 127 and a trigger cover 128.

Similar to the first embodiment, all components, except for the trigger 127 and the trigger cover 128, are located concentrically about a common principal axis of the drive mechanism.

The dial grip 114 is axially constrained to the outer housing 104. It is rotationally constrained, via a splined interface, to the dial member 106. As shown in FIG. 11, the dial member 106 is coupled to the drive member 108 via a ratchet interface (second clutch 119), which occurs on an axial abutment. The ratchet provides a detented position between the dial member 106 and the drive member 108 corresponding to each dose unit, and engages different ramped tooth angles during clockwise and anti-clockwise relative rotation. Corresponding ratchet teeth are provided on facing surfaces of the dial member 106 and the drive member 108.

The display member 107 is rotationally constrained, via a splined interface, to the dial member 106. It is constrained to move along a helical path, relative to the inner housing 105, via a threaded interface. The display member 107 is marked with a sequence of numbers, which are visible through the window 117 in the outer housing 104, to denote the dialled dose of medicament.

The last dose nut 111 is located between the dial member 106 and the drive member 108. It is rotationally constrained to the dial member 106, via a splined interface. It moves along a helical path relative to the drive member 108, via a threaded interface, when relative rotation occurs between the dial member 106 and drive member 108.

The drive member 108 extends from the interface with the dial member 106 down to a ratchet interface with the inner housing 105, which occurs on an axial abutment. The ratchet interface defines the axial position of the drive member 108 at the end of dose delivery, and is included to improve dose accuracy. The drive member 108 is rotationally constrained to the housing via engagement of a set of spline teeth, when the trigger 127 is activated. It provides a clicker arm, which acts radially against a set of ratchet teeth in the inner housing 105. It moves along a helical path relative to the lead screw 109, via a threaded interface. The drive member 108 provides an axial abutment with the inner housing 105, which engages when the drive mechanism dispenses, to react the force applied by the lead screw 109 to the cartridge 103.

The torsion spring 112 is attached at one end to the inner housing 105 and at the other end to the dial member 106. The attachments at both ends are configured to transfer tangential forces, resulting from torsion of the spring 112, and axial forces along the primary axis of the drive mechanism (longitudinal axis). The torsion spring 112 is pre-wound upon assembly, such that it applies a torque to the dial member 106 when the mechanism is at zero units dialled. The action of rotating the dial grip 114, to set a dose, rotates the dial grip 114 relative to the inner housing 105, and winds up the torsion spring 112. The torsion spring 112 is designed in such a way as to exert an axial force which acts to pull the dial member 106 towards the inner housing 105.

The lead screw 109 is rotationally constrained to the inner housing 105 via a splined interface. The lead screw 109 is forced to move axially relative to the inner housing 105, through its threaded interface to the drive member 108, when the drive member 108 moves relative to the inner housing 105. The bearing 110 (washer) is axially constrained to the lead screw 109 and acts on the bung within the liquid medicament cartridge 103.

The inner housing 105 is rigidly constrained to the outer housing 104. The axial abutment with the drive member 108 is provided by a pair of compliant arms which deflect during assembly. A pair of abutment features is provided at either end of the threaded interface with the display member 107, which limit the range of travel of the display member 107. These abutments provide the zero dose and maximum dose stops. The inner housing 105 provides a rotational constraint to the trigger clutch 126, and provides an axial abutment which reacts the axial force generated by the clutch spring 125. The axial position of the trigger clutch 126 is defined by the action of the clutch spring 125, which forces the trigger clutch 26 towards the cartridge end (distal end) of the drive mechanism, and its abutment with the trigger 127. When axially positioned in its at rest position, the trigger clutch 126 engages with the spline teeth on the drive member 108 which constrains the rotation of the drive member 108. The spline teeth on the trigger clutch 126 and the corresponding spline teeth on the drive member 108 form the first clutch 118. Engagement and disengagement of the first clutch 118 is shown in FIGS. 8 and 9.

The clutch spring 125 is located between the inner housing 105 and the trigger clutch 126 and acts to force the trigger clutch 126 towards the cartridge end of the drive mechanism. The trigger 127 is constrained to pivot in the outer housing 104. It has an integral spring element, which acts to rotate the trigger 127 away from the outer housing 104. When the trigger 127 is depressed, an abutment is created with the trigger clutch 126, which moves the trigger clutch 126 axially towards the inner housing 105.

The outer housing 104 provides location for the liquid medication cartridge 103, the pivot for the trigger 127, an interface to rigidly constrain the inner housing 105, a window 117 through which the dose number on the display member 107 can be viewed, and a groove on its external surface to axially retain the dial grip 114. The trigger cover 128 may clip into the outer housing 104, and retains the trigger 127 within its pivot interface with the outer housing 104. The removable cap fits over the cartridge holder element 102 and is retained onto the outer housing 104 via clips when the drive mechanism is not in use. When the cap is fitted onto the outer housing 104, a mechanical interlock is created with the trigger 127, which prevents the trigger 127 from being depressed from its at rest position.

Similar to the first embodiment, display member 107 is provided with a flexible arm 121 on its distal end having an abutment feature 122. Further, the trigger clutch 126 is provided with a corresponding abutment feature 124.

With the device in the at rest condition, the display member 107 is positioned against its zero dose abutment with the inner housing 105 and the trigger 127 is not depressed. Dose marking '0' on the display member 107 is visible through the window 117 on the outer housing 104. As shown in FIGS. 8 and 10, the trigger clutch 126 is in a distal position, which is the position for dose setting and dose resetting.

As the user rotates the dial grip 114, the dial member 106 rotates relative to the drive member 108. Rotation of the dial member 106 generates rotation in the display member 107, which travels along its helical path defined by its interface with the inner housing 105. The device is now set to deliver liquid medicament. The user may now choose to increase the selected dose by continuing to rotate the dial grip 114 in the clockwise direction. With the drive mechanism in a state in which a dose has been selected, the user is able to deselect any number of units from this dose. Deselecting a dose is achieved by the user rotating the dial grip 114 anti-clockwise, which returns the display member 107 towards the zero dose position. However, with the trigger clutch still being in its distal position, abutment features 122, 124 do not contact each other during dose resetting because abutment feature 124 is distally moved out of the track of display member 107 and its abutment feature 122.

With the mechanism in a state in which a dose has been selected, the user is able to activate the drive mechanism to commence delivery of a dose. Delivery of a dose is initiated by the user depressing the trigger 127 on the side of the drive mechanism. As the trigger is depressed, an abutment is created with the trigger clutch 126 which acts to move the trigger clutch axially away from the cartridge 103, i.e. in the proximal direction, against the action of the clutch spring 125. When the trigger 127 is fully depressed, sufficient axial travel has occurred in the trigger clutch 126 to move abutment feature 124 into the path of abutment feature 122 of the display member 107. As the display member 107 approaches its zero dose stop the free end of click-arm 121 rides up a ramp on the abutment feature 124. At the zero position, the click-arm 121 overrides the ramp and returns to its original position providing a tactile and an audible feedback to the user. Thus, the end of dose click features are only engaged during dispensing.

A third embodiment is depicted in FIGS. 12 to 15. The injection device 201 comprises a cartridge 203, a housing 204 and a chassis 205 (inner housing body). A dial gear 206 (dial member) is splined to a number wheel 207 and translated axially by a button 215. Further, the dial gear 206 is splined to a release gear 208 (drive member) during dose dispensing. The number wheel 207 is a display member which displays numbers. A prism 217 is provided which magnifies and reflects the numbers displayed on the number wheel 207. A last dose nut 211 is splined to the dial gear 206 and threaded to the release gear 208. A belt is retained in a belt drum and a ferrule and passes over a roller in the chassis 205. A compression spring 212 is provided as a pre-stressed drive spring acting on a piston rod 209. The spring 212 is fitted between chassis 205 and the ferrule. The release gear 208 is geared to the belt drum and retained in the chassis 205 during dose setting, whereas it is splined to the dial gear 206 during dose dispensing.

A dial 214 which is rotationally coupled to the dial gear via face teeth is rotated clockwise to set a dose. Detents between the dial 214 and a front casework provide discrete dose set positions. The release gear 208 is rotationally fixed by the chassis 205. The number wheel 207 is driven directly from the dial gear 206 with zero dose and maximum dose stops provided between the number wheel and the chassis. The last dose nut 211 is rotated by the dial gear 206 up the thread on the release gear towards a last dose stop. In the similar way, a set dose may be decreased by rotating the dial anti-clockwise.

To dispense a dose, the button 215 is depressed, locking the dial 214. The dial gear 206 engages with the release gear 208 and pushes locking arms of the chassis 205 out of engagement from the release gear 208, allowing this to rotate under the action of the spring 212. Rotation of the release gear 208 allows the belt drum to rotate, releasing the belt and allowing the spring 212 to act on and advance the cartridge bung.

During dose dispensing, i.e. only when the dial gear 206 is pressed against the chassis 205, a ramp feature 222 on the dial gear 206 engages with a clicker arm 223 on the chassis to provide an end of dose click. During dose setting and dose resetting, these features are not engaged, so the 'drop' at the end of dose can be very severe. This is shown as partial section through the chassis 205 and the dial gear 206 in FIGS. 14 and 15. The clicker arm 223 drops off a steep angle ramp and thus creates distinct click sound against dial gear 206.

A fourth embodiment is depicted in FIGS. 16 to 18. Main components of the injection device 301 are a cartridge 303, an outer housing 304, an inner housing body 305, a drive sleeve 308 (drive member), a dial sleeve 306 (dial member), a piston rod in the form of a lead screw 309, a dose dial grip 314 and a spring 312, which is a flat spring or tensioning element.

The spring 312 is provided on two spools between the inner body 305 and the drive sleeve 308. The drive sleeve 308 is rotationally fixed by the inner body 305 during dose setting and dose resetting. The lead screw 309 is splined to the drive sleeve 308 and threaded to the inner body 305. The dial sleeve 306 is coupled to the drive sleeve 308 via a detent and clutched connection. The dose dial grip 314 is splined to the dial sleeve 306 during dose setting and dose resetting. A last dose nut 311 is splined to the dial sleeve 306 and threaded to the drive sleeve 308.

For dose setting the dose dial grip 314 is rotated clockwise by the user. This causes the dial sleeve 306 to rotate, moving a dose nut 307 away from its zero dose stop feature and increasing the dose displayed. In the example of FIG. 16, the dose counter consists of the dial sleeve 306 with printed units and a tens wheel which is incremented by the action of an index gear once per revolution. The last dose nut 311 rotates on a thread on the drive sleeve 308 towards the last dose stop. The drive sleeve 308 is locked by its splined engagement with the housing 304, thus preventing it from being rotated by the spring 312.

To dispense a dose, the dose dial grip 314 is depressed. This disengages the dose dial grip 314 from the dial sleeve 306 so that it does not rotate during dispense. The drive sleeve 308 is moved axially with the dose dial grip 314, disengaging the splined engagement with the inner body 305 allowing the spring 312 to rotate drive sleeve 308. The drive sleeve 308 winds the lead screw 309 forwards through the thread in the inner body 305 to advance the cartridge bung. The odometer counter mechanism and the dose nut 307 then return towards their zero dose positions.

A spring arm 321 with an abutment feature is provided on the dose nut 307. During dose dispensing the spring arm 321 rides over a zero unit stop feature on the dial sleeve and is deflected radially outwards as the dial sleeve 306 rotates anti-clockwise towards the zero dose position. As the zero unit stop passes the end of the spring arm 321, the stored energy is released moving the spring arm 321 inwards radially causing a click as it hits the dial sleeve 306. When dialling up from 0 to 1 unit, the spring arm 321 is forced axially by a ramp on the dial sleeve 306 and back into its unstressed position. This will not create any audible feedback.

An alternative fifth embodiment is shown in FIGS. 19 and 20, wherein the main function and components are as described above with respect to the fourth embodiment. As the dial sleeve 306 rotates anti-clockwise towards zero units a spring arm 323 on dial sleeve 306 is deflected axially by a ramp feature on the dose nut 307. As the ramp feature passes the end of the spring arm 323, the stored energy is released, moving the spring arm 323 axially causing a click as it hits the dose nut 307 thread form. When dialling up from 0 to 1 unit, the spring arm 323 is forced axially by the opposite side of the ramp feature on the dose nut and falls off the edge, but does not contact a surface to cause a click. Throughout the rest of the dose nut 307 stroke, the dose nut 307 traverses away from the spring arm 323 and so they do not come into contact again.

A sixth embodiment is depicted in FIGS. 21 to 23, wherein the main function and components are as described above with respect to the fourth embodiment. Main components of the injection device 401 are a cartridge 403, an outer housing 404, an inner housing body 405, a drive sleeve 408 (drive member), a dial sleeve 406 (dial member), a piston rod in the form of a lead screw 409, a dose dial grip 414 and a spring 412, which is a flat spring or tensioning element. However, in contrast to the fourth embodiment which has the lead screw 309 arranged coaxially with the dial sleeve 306 and the drive sleeve 308, in the sixth embodiment the lead screw 409 is arranged spaced from and parallel to the drive sleeve 408 and the dial sleeve 406. A drive tube 430, which is geared to the drive sleeve 408 is provided as a driven member which is splined to the lead screw 409. Further, a clicker 431, which is splined to the housing 404 and detented to the dial grip 414 is provided coaxially with the drive sleeve 408. The dial sleeve 406 is splined to a number sleeve 407 and is further splined to the dial grip 414 during dose setting and dose resetting.

The dial grip 414 is rotated to set the dose. The dial grip 414 rotates the dial sleeve 406, which in turn rotates the number sleeve 407, causing it to move away from its zero units stop and display the desired dose through a window in the housing 404. The drive sleeve 408 is restrained during dose setting via a splined interface to the housing 404. The spring 412 applies a permanent torque to it. Tactile and audible feedback is provided by the interaction of the dial grip 414 and the clicker 431. The clicker 431 is splined to the housing 404 and shuttles axially under the action of a trigger spring as each dose increment is dialled.

To dispense a dose, the dial grip 414 upper end is pressed by the user. The dial grip 414 first disengages from the dial sleeve 406 so that it does not rotate during dispense. This causes the drive sleeve 408 to be displaced towards the distal end of the device. The drive sleeve 408 then engages with splines on dial sleeve 406. The drive sleeve 408 then disengages from the housing 404, allowing it to be rotated by the spring 412. The drive sleeve 408 rotates the drive tube 430, which in turn rotates the lead screw 409, causing it to advance axially through a thread in the housing 404 and displace the bung in the cartridge.

Feedback at the end of dose is provided by an interaction between the number sleeve 407 and the clicker 431. The clicker 431 moves between two distinct axial positions for dose setting or resetting and dose dispensing. This allows a compliant feature 424 on the clicker 431 to interact with a feature 422 on the number sleeve 407 during dispensing but not during dialling so that the dial torque is not affected.

The invention claimed is:

1. A drive mechanism for an injection device, the drive mechanism comprising:
- a housing;
- a dosing member rotatable relative to the housing between a zero dose position and a maximum dose position during dose setting, dose resetting, and dose dispensing; and
- an insert rotationally constrained to the housing and axially movable between a dose dispensing position and a dose setting and resetting position,
- wherein the dosing member comprises at least one abutment feature configured to contact at least one abutment feature of the insert when the dosing member reaches the zero dose position during the dose dispensing,
- wherein at least one of an audible feedback and a tactile feedback is generated when the at least one abutment feature of the dosing member contacts the at least one abutment feature of the insert, and
- wherein the at least one abutment feature of the insert is configured to contact the at least one abutment feature of the dosing member only when the insert is in the dose dispensing position.

2. The drive mechanism according to claim 1, wherein the at least one abutment feature of the insert is configured to contact the at least one abutment feature of the dosing member only during the dose dispensing when the dosing member reaches the zero dose position.

3. The drive mechanism according to claim 1, wherein the insert is configured to radially deflect one of the at least one abutment feature of the dosing member and the at least one abutment feature of the insert when the insert is in the dose dispensing position.

4. The drive mechanism according to claim 1, wherein the insert comprises an inner body rotationally constrained to the housing the dosing member comprises a number sleeve in threaded engagement with the housing or the inner body and movable between a zero dose position and a maximum dose position, and
- wherein the inner body comprises a flexible arm having a first abutment feature and the number sleeve comprises a corresponding second abutment feature configured to contact the first abutment feature when the number sleeve reaches the zero dose position during the dose dispensing.

5. The drive mechanism according to claim 1, wherein the insert comprises a trigger clutch rotationally constrained to the housing and the dosing member comprises a number sleeve in threaded engagement with the housing or an inner body and movable between a zero dose position and a maximum dose position, and
- wherein the trigger clutch comprises a first abutment feature and the number sleeve comprises a corresponding second abutment feature configured to contact the first abutment feature when the number sleeve reaches the zero dose position during the dose dispensing.

6. The drive mechanism according to claim 5, wherein the number sleeve and the second abutment feature are configured to move on a helical path during the dose setting, the dose resetting, and the dose dispensing, and wherein the first abutment feature is in the helical path only during the dose dispensing.

7. The drive mechanism according to claim 6, further comprising:
- a trigger for axially displacing the trigger clutch relative to the housing between a dose setting position and a dose dispensing position,
- wherein the first abutment feature is not in the helical path in the dose setting position of the trigger clutch, and
- wherein the trigger urges the trigger clutch in the dose dispensing position and the first abutment feature into the helical path.

8. The drive mechanism according to claim 1, wherein the insert comprises an inner body rotationally constrained to the housing,
- the dosing member comprises a number sleeve in threaded engagement with the housing or the inner body and movable between a zero dose position and a maximum dose position, wherein the inner body comprises a flexible arm having a first abutment feature and the number sleeve comprises a corresponding second abutment feature configured to contact the first abutment feature when the number sleeve reaches the zero dose position during the dose dispensing; and
- the insert comprises a drive member axially displaceable relative to the housing between a dose setting position and a dose dispensing position,
- wherein the first abutment feature is not in a helical path in an unstressed state of the flexible arm, and
- wherein, in the dose dispensing position, the drive member is configured to urge the flexible arm and the first abutment feature into the helical path.

9. The drive mechanism according to claim 1, wherein the insert comprises a dose nut axially displaceable between a zero dose position and a maximum dose position and rotationally constrained to the housing; and
- the dosing member comprises a dial sleeve rotatable relative to the housing,
- wherein the dose nut comprises a flexible finger with a first abutment feature, which is deflected during the dose dispensing and which hits a second abutment feature provided on the dial sleeve when the dose nut reaches the zero dose position.

10. The drive mechanism according to claim 1, wherein the insert comprises a dose nut axially displaceable between a zero dose position and a maximum dose position and rotationally constrained to the housing; and
- the dosing member comprises a dial sleeve rotatable relative to the housing, wherein the dial sleeve comprises a flexible finger with a first abutment feature, which is deflected during the dose dispensing and which hits a second abutment feature provided on the dose nut when the dose nut reaches the zero dose position.

11. The drive mechanism according to claim 1, wherein the insert comprises a clicker rotationally constrained to the housing; and the dosing member comprises a number sleeve in threaded engagement with the housing or an inner body and movable between a zero dose position and a maximum dose position, wherein the clicker comprises a first abutment feature and the number sleeve comprises a corresponding second abutment feature contacting the first abutment feature when the number sleeve reaches the zero dose position during the dose dispensing.

12. The drive mechanism according to claim 11, wherein the number sleeve and the second abutment feature are configured to move on a helical path during the dose setting, the dose resetting, and the dose dispensing, and wherein the clicker is axially displaceable relative to the housing such that the first abutment feature is in the helical path only during the dose dispensing.

13. The drive mechanism according to claim 12, further comprising a dial grip sleeve axially displaceable relative to the housing between a dose setting position and a dose dispensing position, wherein the first abutment feature is not in the helical path in the dose setting position of the dial grip sleeve, and wherein, in the dose dispensing position, the dial grip sleeve is configured to axially displace the clicker to urge the first abutment feature into the helical path.

14. An injection device comprising:
a cartridge containing a medicament; and
a drive mechanism comprising
housing;
a dosing member rotatable relative to the housing between a zero dose position and a maximum dose position during dose setting, dose resetting, and dose dispensing; and
an insert rotationally constrained to the housing and axially movable between a dose dispensing position and a dose setting and resetting position, wherein the dosing member and the insert each comprises at least one abutment feature contacting each other when the dosing member reaches the zero dose position during dose dispensing, wherein at least one of an audible feedback and a tactile feedback is generated by the contact of the at least one abutment feature of the dosing member and the at least one abutment feature of the insert, and wherein the at least one abutment feature of the insert is configured to contact the at least one abutment feature of the dosing member only when the insert is in the dose dispensing position.

15. The injection device according to claim 14, wherein the at least one abutment feature of the insert is configured to contact the at least one abutment feature of the dosing member only during the dose dispensing when the dosing member reaches the zero dose position.

16. The injection device according to claim 14, wherein the insert is configured to radially deflect one of the at least one abutment feature of the dosing member and the at least one abutment feature of the insert when the insert is in the dose dispensing position.

17. A method of operating an injection device, the method comprising:
setting a dose such that a dosing member rotates relative to a housing of the injection device between a zero dose position and a position below or equal to a maximum dose position; and
dispensing the dose such that at least one abutment feature of the dosing member contacts at least one abutment feature of an insert when the dosing member reaches the zero dose position, thereby generating at least one of an audible feedback and a tactile feedback, the insert being rotationally constrained to the housing of the injection device,
wherein dispensing the dose comprises axially moving the insert from a dose setting position to a dose dispensing position, such that the at least one abutment feature of the dosing member contacts the at least one abutment feature of the insert only when the insert is in the dose dispensing position, and wherein the insert is rotationally contained to the housing.

18. The method of claim 17, wherein dispensing the dose comprises displacing a trigger from a dose setting position to a dose dispensing position, thereby urging the at least one abutment feature of the insert into a helical path.

* * * * *

UNITED STATES PATENT AND TRADEMARK OFFICE
CERTIFICATE OF CORRECTION

PATENT NO. : 10,238,807 B2  
APPLICATION NO. : 14/915441  
DATED : March 26, 2019  
INVENTOR(S) : David Aubrey Plumptre and Simon Lewis Bilton Page 1 of 1

It is certified that error appears in the above-identified patent and that said Letters Patent is hereby corrected as shown below:

In the Claims

In Column 23, Line 49, Claim 4, after "housing" insert -- , --

In Column 23, Line 61, Claim 5, after "housing" insert -- , --

In Column 25, Line 39 (approx.), Claim 14, before "housing;" insert -- a --

Signed and Sealed this  
First Day of October, 2019

Andrei Iancu  
*Director of the United States Patent and Trademark Office*

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: insulin analogue/derivative

<400> SEQUENCE: 1
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20              25                  30

Ser Gly Ala Pro Pro Pro Ser
        35
```